US011369341B2

(12) United States Patent
Renaud et al.

(10) Patent No.: US 11,369,341 B2
(45) Date of Patent: Jun. 28, 2022

(54) METHOD FOR CHARACTERISING BONE USING ULTRASONIC WAVES

(71) Applicants: SORBONNE UNIVERSITE, Paris (FR); CENTRE NATIONAL DE LA RECHERCHE SCIENTIFIQUE (CNRS), Paris (FR); INSTITUT NATIONAL DE LA SANTE ET DE LA RECHERCHE MEDICALE (INSERM), Paris (FR); ECOLE SUPERIEURE DE PHYSIQUE ET DE CHIMIE INDUSTRIELLES DE LA VILLE DE PARIS, Paris (FR)

(72) Inventors: Guillaume Renaud, Paris (FR); Didier Cassereau, Clamart (FR)

(73) Assignees: SORBONNE UNIVERSITE, Paris (FR); CENTRE NATIONAL DE LA RECHERCE SCIENTIFIQUE (CNRS), Paris (FR); INSTITUT NATIONAL DE LA SANTE ET DE LA RECHERCHE MEDICALE (INSERM), Paris (FR); ECOLE SUPERIEURE DE PHYSIQUE ET DE CHIMIE INDUSTRIELLES DE LA VILLE DE PARIS, Paris (FR)

( * ) Notice: Subject to any disclaimer, the term of this patent is extended or adjusted under 35 U.S.C. 154(b) by 198 days.

(21) Appl. No.: 16/632,290

(22) PCT Filed: Jul. 19, 2018

(86) PCT No.: PCT/EP2018/069688
§ 371 (c)(1),
(2) Date: Mar. 5, 2020

(87) PCT Pub. No.: WO2019/016339
PCT Pub. Date: Jan. 24, 2019

(65) Prior Publication Data
US 2020/0359992 A1 Nov. 19, 2020

(30) Foreign Application Priority Data

Jul. 19, 2017 (FR) .................................... 1756864

(51) Int. Cl.
*A61B 8/08* (2006.01)
*G16H 30/40* (2018.01)
(Continued)

(52) U.S. Cl.
CPC .............. *A61B 8/0875* (2013.01); *A61B 8/14* (2013.01); *A61B 8/463* (2013.01); *A61B 8/485* (2013.01);
(Continued)

(58) Field of Classification Search
CPC ... A61B 8/0875; A61B 8/5223; A61B 8/4444; A61B 8/54; A61B 8/14; A61B 8/469;
(Continued)

(56) References Cited

U.S. PATENT DOCUMENTS 5,038,787 A 8/1991 Antich et al.
2005/0004457 A1 1/2005 Moilanen et al.
(Continued)

FOREIGN PATENT DOCUMENTS

EP 0873516 B1 * 12/2005 ............... G01H 5/00

OTHER PUBLICATIONS

C. M. Langton et al., "A contact method for the assessment of ultrasonic velocity and broadband attenuation in cortical and cancellous bone," Clinical Physics and Physiological Measurement, vol. 11, No. 3, pp. 243-249, Jul. 1990 (Year: 1990).*
(Continued)

*Primary Examiner* — Oommen Jacob
*Assistant Examiner* — Nyrobi Celestine
(74) *Attorney, Agent, or Firm* — Womble Bond Dickinson (US) LLP

(57) ABSTRACT

The invention relates to a method for characterising bone, the method comprising the steps of receiving (102) ultra-
(Continued)

sonic wave echo signals transmitted into a body, determining (104) a speed of sound in the body's non-bone biological tissue, locating (106) a first demarcation curve between non-bone biological tissue and bone in an image of the body constructed during said determining step, and determining (108) a speed of sound in bone. The steps of determining speed include constructing images from the signals, and a metric calculation indicative of a focus quality in the constructed images.

15 Claims, 9 Drawing Sheets

(51) Int. Cl.
    *A61B 8/14*     (2006.01)
    *A61B 8/00*     (2006.01)
    *G06T 7/10*     (2017.01)

(52) U.S. Cl.
    CPC .............. *A61B 8/5223* (2013.01); *A61B 8/56* (2013.01); *G06T 7/10* (2017.01); *G16H 30/40* (2018.01)

(58) Field of Classification Search
    CPC ..... A61B 8/4254; A61B 8/461; A61B 8/4547; A61B 8/5207; A61B 8/5269; G16H 30/40
    See application file for complete search history.

(56) References Cited

U.S. PATENT DOCUMENTS

| | | | | |
|---|---|---|---|---|
| 2010/0185086 A1* | 7/2010 | Suetoshi | .............. | A61B 8/0875 600/438 |
| 2010/0185089 A1* | 7/2010 | Gourevitch | .......... | A61B 8/0875 600/443 |
| 2010/0210943 A1* | 8/2010 | Mahmoud | ................ | A61B 8/14 600/437 |
| 2011/0092818 A1* | 4/2011 | Sarvazyan | ........... | A61B 8/4461 600/449 |
| 2011/0270136 A1* | 11/2011 | Vitek | ....................... | A61N 7/02 601/2 |
| 2015/0211844 A1* | 7/2015 | Cretin | .................. | A61B 8/0858 702/171 |
| 2015/0342568 A1* | 12/2015 | Kato | ..................... | A61B 8/5207 600/443 |
| 2016/0106392 A1* | 4/2016 | Manbachi | ............ | A61B 8/4494 600/439 |

OTHER PUBLICATIONS

S. Ye et al., "Ultrasound shear wave imaging," AIP Conference Proceedings, vol. 509, pp. 847-851, Nov. 2000 (Year: 2000).*
J. G. Berryman, "Exact Seismic Velocities for VTI and HTI Media and Extended Thomsen Formulas for Stronger Anisotropies," Geophysics, vol. 73, No. 1, pp. 1-22, Jan. 2008 (Year: 2008).*
M. Daugschies et al., "The preliminary evaluation of a 1 MHz ultrasound probe for measuring the elastic anisotropy of human cortical bone," Ultrasonics, vol. 54, pp. 4-10, Jul. 2013 (Year: 2013).*
Bochud et al., "Predicting bone strength with ultrasonic guided waves", Scientific Reports, vol. 7, Mar. 3, 2017, pp. 1-14.
International Preliminary Report on Patentability received for PCT Patent Application No. PCT/EP2018/069688, dated Jan. 30, 2020, 13 pages (7 pages of English Translation and 6 pages of Original Document).
International Search Report and Written Opinion received for PCT Patent Application No. PCT/EP2018/069688, dated Aug. 30, 2018, 17 pages (8 pages of English Translation and 9 pages of Original Document).
Napolitano et al., "Sound Speed Correction in Ultrasound Imaging", Ultrasonics, vol. 44, Dec. 2006, 16 pages.
Preliminary Research Report received for French Application No. 1756864, dated May 14, 2018, 4 pages (1 page of French Translation Cover Sheet and 3 pages of original document).
Treeby et al., "Automatic sound speed selection in photoacoustic image reconstruction using an autofocus approach," Journal of Biomedical Optics, vol. 16, No. 9, Sep. 2011, pp. 090501-1-090501-3.

* cited by examiner

| | |
|---|---|
| Construction of second images from the first echo signals and using first candidate values for $V_{bone1}$ and from $V_{tissue1}$ and the first demarcation curve | 300 |
| For each second image, calculating a second focus quality metric in the second image | 302 |
| Selecting one of the second candidate values as the velocity $V_{bone1}$ based on the calculated second metrics | 304 |

METHOD FOR CHARACTERISING BONE USING ULTRASONIC WAVES

FIELD OF THE INVENTION

The present invention relates to a method for characterizing bone.

PRIOR ART

The use of waves to characterize a living body is widely known.

X-ray tomography imaging is, for example, a medical imaging technique using X-rays that pass through the body to be imaged. However, this technique has the disadvantage of exposing the body to potentially dangerous ionizing radiation. Still day, we avoid exposing young children's bodies to such X-rays unless absolutely necessary.

Other known techniques for characterizing a living body use ultrasonic waves, which are less dangerous than X-rays.

Ultrasonic waves are conventionally emitted by an array of transceivers, and their echoes on a body to be characterized are received by the same or another array after a certain propagation time between emission and reception.

Images showing a section of the body in which the ultrasonic waves have propagated can then be constructed based on the echo signals received by the transceiver array(s).

During the construction of such images, it is assumed that the body is a homogeneous medium, and that, consequently, the sound velocity is uniform in the body under study.

The sound velocity chosen is usually an average sound velocity in non-bone biological tissue (for example skin or muscle), which is generally of the order of 1540 metres per second with an error of about 5-10%. The images obtained on the basis of this assumption thus have a satisfactory quality in regions of interest showing non-bone biological tissue.

However, the sound velocity in bone (generally between 2800 metres per second and 4200 metres per second for a compressional wave in cortical bone) is much higher than the sound velocity in non-bone biological tissue. Images obtained on the basis of a uniform velocity assumption whose value corresponds to a sound velocity in non-bone biological tissue show poor quality in regions of interest showing bone. This poor quality typically results in low intensity and blurred bone. For this reason, it is a common misconception in the medical community that ultrasound waves "do not penetrate easily" into bone.

The difference between the sound velocity in a bone and in the non-bone biological tissues surrounding the bone creates a refractive effect. It is therefore not possible to reconstruct good quality images based on a predetermined value of sound velocity in bone, as has already been done with sound velocity in non-bone biological tissue.

The sound velocity in a bone depends on several factors.

First, the sound velocity in a bone varies from one individual to another. This is why it is very useful information for the subsequent diagnosis of disorders such as osteoporosis.

Secondly, the sound velocity in a bone is not the same in all directions. Bone is indeed an anisotropic medium. This is due in particular to the fact that the so-called cortical bone comprises channels extending parallel to the longitudinal axis of a long bone (for example tibia) to accommodate blood vessels. Thus, a compressional sound wave propagates through a bone in a direction parallel to the longitudinal axis of a long bone faster than in another direction.

Ultimately, determining the precise sound velocity is a major challenge in characterizing bone.

In this respect, a method for determining the sound velocity in a bone parallel to the longitudinal axis of the bone has already been proposed. During this method, ultrasonic waves are emitted by an array of ultrasonic wave transceivers aligned parallel to the longitudinal axis of a long bone. On the basis of echo signals received by the receivers, a velocity of a bone-guided wave, known as the head wave, propagating along the outer surface of the bone is determined. This velocity is determined fairly easily by assuming that the relationship between the instant of reception of an ultrasonic wave by one of the receivers and the distance between that receiver and the transmitter of the same wave is a linear function.

However, this method cannot be used to determine a sound velocity in bone in any direction other than a direction parallel to the longitudinal axis of a long bone. Consequently, it can only partially characterize a bone.

DISCLOSURE OF THE INVENTION

A purpose of the invention is to provide a method that can be used to more completely characterize a bone.

The invention therefore proposes a method for characterizing bone, the method comprising the steps of:
  emission of first ultrasonic waves to a body comprising bone and non-bone biological tissue surrounding the bone,
  reception of first echo signals of the first ultrasonic waves emitted,
  determination of a sound velocity in non-bone biological tissue in a first direction, the determination comprising substeps of:
    for several first predetermined candidate values, construction of a first image showing the non-bone biological tissue and the periosteum of the bone, from the first echo signals and under the assumption that the sound velocity in the non-bone biological tissue in the first direction is equal to the first candidate value,
    for each first image, calculation of at least one first metric indicative of a focus quality of the periosteum and/or the non-bone biological tissue surrounding the bone in the first image,
    selection of one of the first candidate values as sound velocity in the non-bone biological tissue in the first direction, based on the first metrics,
  localization of a first demarcation curve between the non-bone biological tissue and the bone in one of the first images,
  determination of a sound velocity in the bone in the first direction, the determination comprising substeps of:
    for several predetermined second candidate values, construction of a second image showing cortical bone tissue of the bone and the endosteum, from the first echo signals, the sound velocity in the non-bone biological tissue in the first determined direction, and the first demarcation curve, and under the assumption that the sound velocity in the bone in the first direction is equal to the second candidate value,
    for each second image, calculation of at least one second metric indicative of a focus quality of the cortical bone tissue of the bone and/or the endosteum in the second image, selection of one of the second candidate values as the sound velocity in the bone in the first direction, based on the second metrics.

The proposed method may also include the following optional features or steps, taken alone or in combination where technically feasible.

The construction of a first image using a first candidate value may include the following steps implemented for at least one point of the non-bone biological tissue:
estimation of first trajectories of first ultrasonic waves emitted by transmitters, then passed through the point of the non-bone biological tissue, then received by receivers, from the first echo signals, under the assumption that the sound velocity in the non-bone biological tissue in the first direction is equal to the first candidate value,
calculation of propagation times of ultrasonic waves via the first estimated trajectories,
calculation of an intensity of a pixel of the first image at the point of the non-bone biological tissue, based on propagation times, first echo signals and positions of transmitters and receivers.

The construction of a second image using a second candidate value involves the following steps implemented for at least one point on the bone:
estimation of second trajectories of first ultrasonic waves emitted by transmitters, then passed through the point of the bone, then received by receivers, from the echo signals, based on the sound velocity in the non-bone biological tissue in the first determined direction of the first demarcation curve, and under the assumption that the sound velocity in the bone in the first direction is equal to the second candidate value,
calculation of propagation times of ultrasonic waves via the second estimated trajectories,
calculation of an intensity of a pixel of the second image at the bone point, based on propagation times, first echo signals and transmitter and receiver positions.

The localization of the first demarcation curve can be implemented in the first image that has been constructed using the first value selected as the sound velocity in the non-bone biological tissue in the first direction.

The first ultrasonic waves can be waves emitted by transmitters and echo signals received by receivers aligned along an axis perpendicular to a longitudinal axis of the bone, and wherein the first direction is a direction perpendicular to the longitudinal axis of the bone.

The method may include a display of the first image constructed using the first selected value, and/or the second image constructed using the second selected value.

The method may also include steps of:
emission of second ultrasonic waves to the body,
reception of echo signals of the emitted second ultrasonic waves, so-called second echo signals,
determination of a sound velocity in non-bone biological tissue in a second direction different from the first direction, comprising substeps of:
for several third candidate values, construction of a third image showing the non-bone biological tissue and the periosteum of the bone, from the second echo signals and under the assumption that the sound velocity in the non-bone biological tissue in the second direction is equal to the second candidate value,
for each third image, calculation of at least one third metric indicative of a focus quality of the periosteum and/or of the non-bone biological tissue in the third image,
selection of one of the third candidate values as the sound velocity in non-bone biological tissue in the second direction, based on the third metrics,
localization of a second demarcation curve between the non-bone biological tissue and the periosteum in one of the third images,
determination of a sound velocity in the bone in the second direction, using the second echo signals,
determination of a bone anisotropy parameter that can be used by a predetermined function in combination with the sound velocity in the bone in the first direction and the sound velocity in the bone in the second direction to calculate a sound velocity in the bone in any direction, the determination of the anisotropy parameter comprising substeps of:
for a plurality of predetermined fourth candidate values, construction of a fourth image showing cortical bone tissue and the endoskeleton of the bone, from the second echo signals, the sound velocity in the bone in the first direction, the second demarcation curve, the sound velocity in the non-bone biological tissue in the second direction, and optionally the sound velocity in the bone in the second direction, the predetermined function, and assuming that the anisotropy parameter of the bone is equal to the fourth candidate value,
for each fourth image, calculation of a fourth metric indicative of a focus quality of the endosteum and/or the cortical bone tissue of the bone in the fourth image,
selection of one of the fourth candidate values as a parameter of bone anisotropy, based on the fourth metrics.

The construction of a fourth image may include the following steps implemented for at least one point on the bone:
estimation of third trajectories of second ultrasonic waves emitted by transmitters, then passed through the point of the bone, then received by receivers, from the second echo signals, of the sound velocity in the non-bone biological tissue, and optionally the sound velocity in the bone in the first determined direction, the sound velocity in the bone in the second determined direction, the second demarcation curve, the predetermined function and under the assumption that the anisotropy parameter of the bone is equal to the fourth candidate value,
calculation of propagation times of ultrasonic waves via the third estimated trajectories,
calculation of an intensity of a pixel of the fourth image at the bone point, based on propagation times and second echo signals and transmitter and receiver positions.

The localization of the second demarcation curve can be implemented in the third image that has been constructed using the third value selected as the sound velocity in the non-bone biological tissue in the second direction.

The method may include a display of the third image constructed using the third selected value, and/or the fourth image constructed using the fourth selected value and the sound velocity in the bone in the second direction.

The second ultrasonic waves may be waves emitted by transmitters and the second echo signals are received by receivers aligned along an axis lying in a plane which otherwise includes a longitudinal axis of the bone, and wherein the second direction is preferably a direction parallel to the longitudinal axis of the bone.

The or each sound velocity in the bone determined may be a compressional wave propagation velocity or a shear wave propagation velocity.

The or each sound velocity in the bone determined is a compressional wave propagation velocity, and the predetermined function is a function V of the form:

$$V(\theta)=V_{bone2}-(V_{bone2}-V_{bone1})[\beta \sin^2(\theta) \cos^2(\theta)+\cos^4(\theta)]$$

wherein $V_{bone1}$ is the propagation velocity of compressional waves in the bone in the first determined direction, $V_{bone2}$ is the propagation velocity of compressional waves in the bone in the second determined direction, $\beta$ is the anisotropy parameter of the bone, $\theta$ is an angle, $V(\theta)$ is a propagation velocity of compressional waves in the bone in a direction forming the angle $\theta$ with the first direction.

The sound velocity in the bone in the first determined direction may be a shear wave propagation velocity, and the predetermined function may be a function V of the form:

$$V(\theta)=V_{bone1}[1+\beta \sin^2(\theta) \cos^2(\theta)]$$

wherein $V_{bone1}$ is the propagation velocity of shear waves in the bone in the first determined direction, $\beta$ is the anisotropy parameter of the bone, $\theta$ is an angle, $V(\theta)$ is a velocity of shear wave propagation in the bone in a direction forming the angle $\theta$ with the first direction.

It is possible to determine, in conjunction with the sound velocity in the bone in the first direction, a bone anisotropy parameter that can be used by a predetermined function in combination with the sound velocity in the bone in the first determined direction to calculate a sound velocity in the bone in any direction, said joint determination comprising substeps of:

for a plurality of pairs of predetermined second and fourth candidate values, construction of a second image showing cortical bone tissue of the bone and the endosteum of the bone, from the first echo signals, the sound velocity in the non-bone biological tissue in the first determined direction, and the first demarcation curve, under the assumption that the sound velocity in the bone in the first direction is equal to the second candidate value, and under the assumption that the anisotropy parameter of the bone is equal to the fourth candidate value, for each second image, calculation of at least one second metric indicative of a focus quality of the cortical bone tissue of the bone and/or the endosteal bone in the second image, joint selection of a second candidate value as the sound velocity in the bone in the first direction and a fourth candidate value as a parameter of bone anisotropy, the selection being carried out according to the second metrics.

DESCRIPTION OF THE FIGURES

Other characteristics, purposes and advantages of the invention will become apparent from the following description, which is purely illustrative and non-limiting, and which should be read in conjunction with the appended drawings in which.

Similar elements have identical reference marks throughout the figures.

DETAILED DESCRIPTION OF EMBODIMENTS OF THE INVENTION

Figure 1:
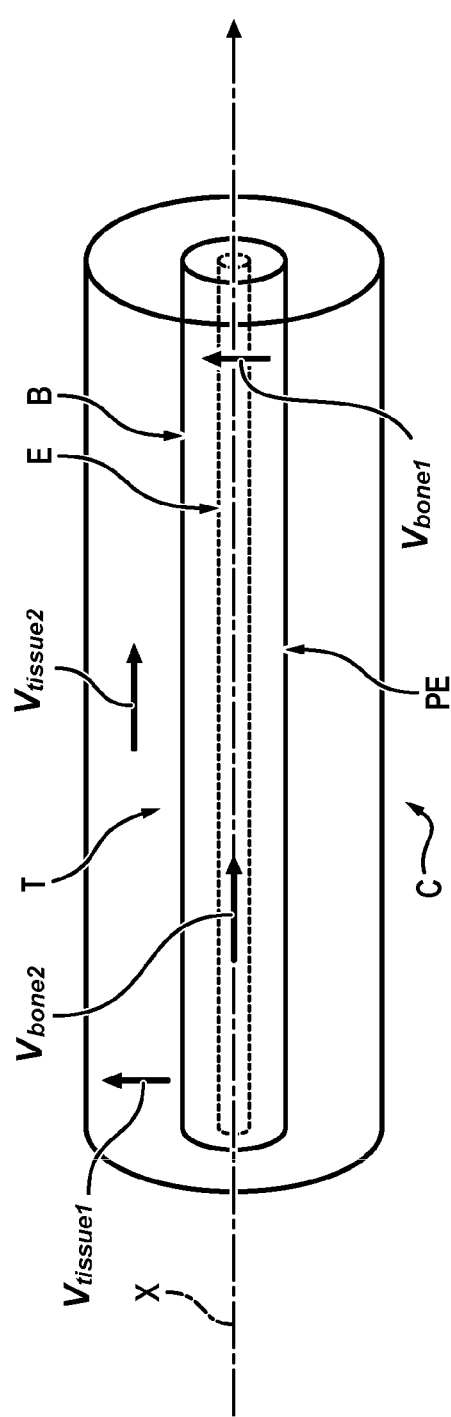
FIG. 1 is a schematic perspective view of a body containing bone.

FIG. 1 is a schematic representation of an example of a body part C comprising a bone B and non-bone biological tissue T.

The bone B extends along a longitudinal axis X. The bone B includes in particular bone marrow, an endosteum E extending around the marrow (dotted line in FIG. 1), and a periosteum PE that surrounds the endosteum E. The periosteum PE is an outer layer of the bone B. The bone B also includes cortical bone tissue between the endosteum E and the periosteum PE.

The non-bone biological tissue T extends around the bone, and more specifically around the periosteum PE with which it is in contact.

The non-bone biological tissue T includes flesh or even skin surrounding the flesh.

It is well known that ultrasonic waves can propagate in such a body C.

In this respect, FIG. 1 shows several wave propagation velocities, which are as follows:

$V_{bone1}$: propagation velocity of a compressional wave in the bone B in a direction perpendicular to the longitudinal axis X of the bone B (this is referred to as the "radial direction", and "radial" compressional waves), $V_{bone2}$: propagation velocity of a compressional wave in the bone B in a direction parallel to the longitudinal axis X (this is referred to as the "axial" direction and "axial" compressional waves), $V_{tissue1}$: propagation velocity of a compressional wave in the non-bone biological tissue T in a direction perpendicular to a longitudinal axis of a bone, $V_{tissue2}$: propagation velocity of a compressional wave in the non-bone biological tissue T in a direction parallel to the longitudinal axis X of the bone B.

The propagation of compressional waves in a bone in any direction can be calculated by means of a predetermined function V combining an anisotropic parameter) β and velocities $V_{bone2}$ and $V_{bone1}$.

The predetermined function V is then typically of the following form:

$$V(\theta) = V_{bone2} - (V_{bone2} - V_{bone1})[\beta \sin^2(\theta)\cos^2(\theta) + \cos^4(\theta)]$$

where

θ is any angle,

β is a parameter of bone anisotropy,

V(θ) is a sound velocity in the bone B in a direction forming the angle θ with the first direction.

This function V is based on the relatively realistic assumption that the bone B is transverse isotropic, i.e. isotropic in a plane perpendicular to its longitudinal axis X.

Figure 2:
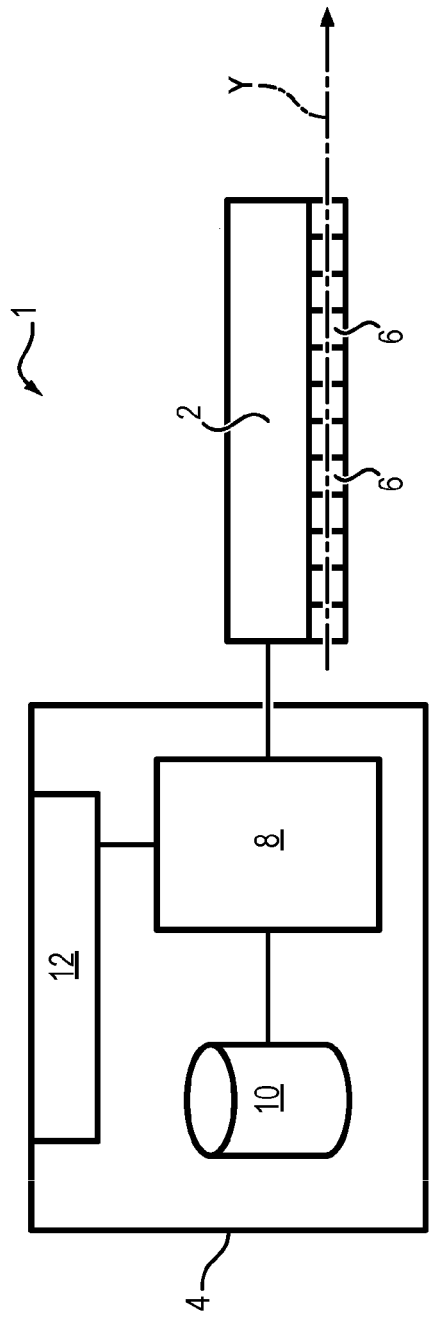
FIG. 2 is a schematic representation of a system for characterizing a bone, according to an embodiment of the invention.

With reference to FIG. 2, a characterization system 1 comprises an ultrasonic probe 2, a device 4 for processing the echo signals acquired by the probe 2, or even a display 12.

The ultrasonic probe 2, known per se, comprises at least one array of transceivers 6 aligned along an axis Y.

Conventionally, the probe 2 includes a silicone lens (not shown) arranged in front of the array of transceivers 6.

Each transceiver 6 is adapted to transmit ultrasonic waves.

Each transceiver 6 is also adapted to acquire echo signals of ultrasonic waves emitted by any other transceiver 6.

The relative positions of the transceivers 6 are predetermined. Typically, the transceivers 6 are spaced a constant pitch along the axis of the probe 2.

In addition, the echo signal processing device 4 conventionally comprises at least a processor 8 and a memory 10.

The processor 8 is configured to perform calculations, in particular an image processing algorithm, the operation of which will be detailed hereinbelow.

The memory 10 stores predetermined data. These data are not specific to the body of an individual but are generic data applicable to any individual in a population.

The predetermined data includes a set of first predetermined candidate values for the velocity $V_{tissue1}$. The first predetermined candidate values are typically between 1400 and 1700 meters per second.

The predetermined data also includes a set of second candidate values for velocity $V_{bone1}$. The second predetermined candidate values are typically between 2600 and 3600 meters per second.

The predetermined data includes a set of third predetermined candidate values for velocity $V_{tissue2}$. The third predetermined candidate values are typically between 1400 and 1700 metres per second.

The predetermined data also includes a set of fourth candidate values for the parameter β of anisotropy of the bone B. The fourth values are typically between 0.8 and 2.

As will be seen hereinbelow, the algorithm implemented by the processor 8 assumes that the propagation velocity in the bone B is governed by the function V described above, which depends in particular on the parameter β of anisotropy.

Figure 3:
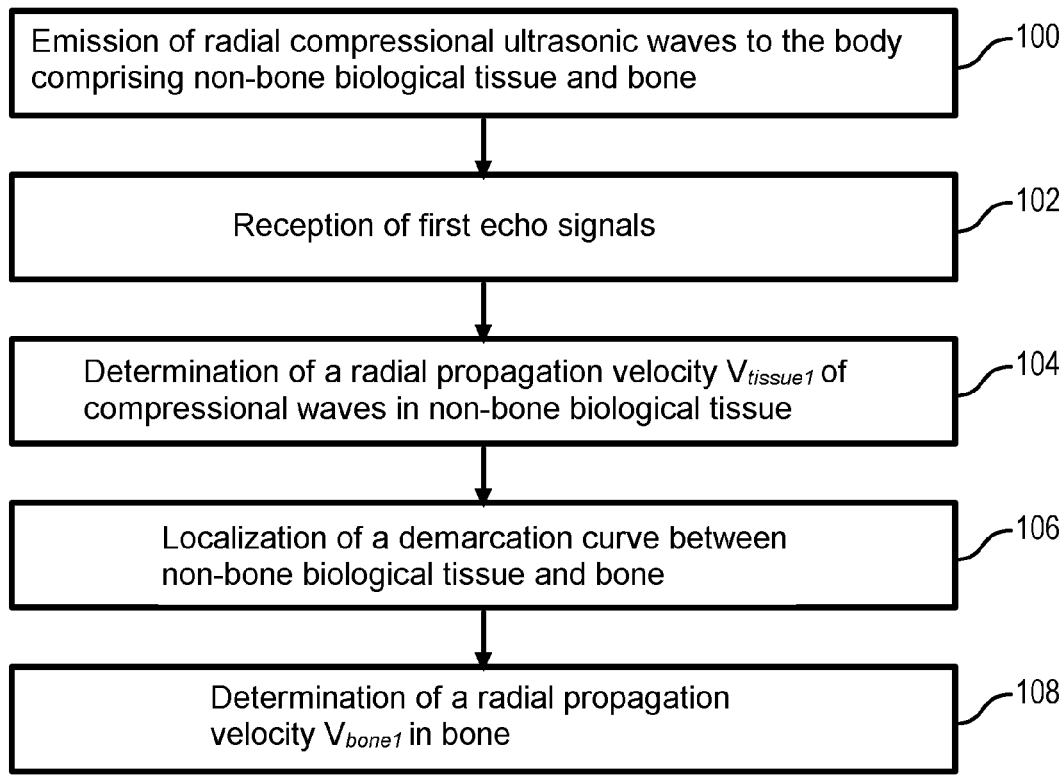
FIG. 3 shows certain steps of a method for characterizing a bone, according to a first embodiment of the invention.

With reference to the flowchart in FIG. 3, a method for characterizing the bone B shown in FIG. 1 using the characterization system 1 comprises the following steps.

The probe 2 is positioned close to the body C in a first position.

In the first position, the transceivers 6 of the probe 2 are aligned substantially perpendicular to the longitudinal axis of the bone B. In other words, the axis Y of the probe 2 is perpendicular to the axis X of the bone B in the first position.

The probe 2 emits first ultrasonic waves to the body C in a first direction towards (step 100).

The first waves are, for example, radial compressional waves. In other words, the first direction is a direction perpendicular to the longitudinal axis of the bone B.

The first ultrasonic waves penetrate the body C and are reflected by it at different depths into the body C.

Echo signals from these waves, called first echo signals hereinafter, are thus acquired by the transceivers of the probe 2 (step 102). Of course, a wave emitted by a transceiver 6 of index i can perfectly well give rise to an echo signal received by another transceiver 6 of index j.

The first echo signals are digitized, transmitted to processing device 4 and stored in the memory 10 in a known form of the prior art.

The processor 8 determines the velocity $V_{tissue1}$ based on the first echo signals received and based on the first predetermined values stored in the memory 10 (step 104).

Figure 4:
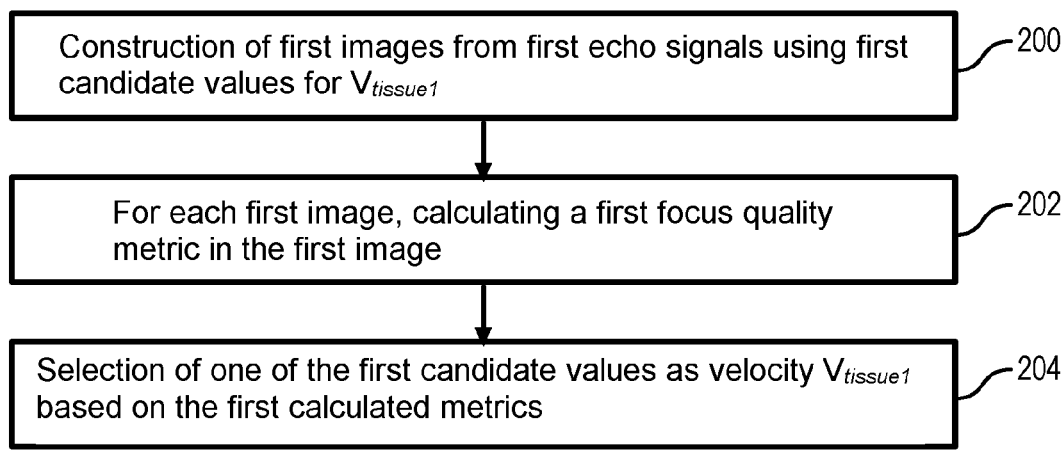
FIGS. 4 and 6 detail substeps of steps of the method according to the first embodiment of the invention.

With reference to FIG. 4, the determination of the velocity 104 $V_{tissue1}$ includes the following substeps.

The processor 8 constructs an image, called first image hereinafter, from the first echo signals, assuming that the velocity $V_{tissue1}$ is equal to a first candidate value (step 200).

The first image consists of a grid of pixels, each pixel being defined by a position in the grid and by an intensity I, this intensity being typically representative of a grey level. The first image also represents a sectional view of the body C in a plane in which the first ultrasonic waves propagated (this sectional plane being parallel to the axis of the probe 2). Each point of this cut plane will thus be shown in a pixel of the first image.

In a preferred embodiment, the construction of the first image is carried out by means of the Kirchhoff migration method or the so-called "Total Focusing Method". These methods are known per se, but advantageously applied to the first ultrasonic signals previously acquired.

The construction 200 of the first image using one of these known methods includes the following substeps.

For a given point P of the body C under study, the processor 8 estimates the trajectories of the first ultrasonic waves emitted by the transmitters, then passed through the point P, then received by receivers, from the first echo signals, under the assumption that the velocity $V_{tissue1}$ is equal to one of the first candidate values.

The ultrasonic waves passing through the point P were each transmitted by a transmitter of index i, whose position is known along the axis Y of the probe 2, and received by a receiver of index j, whose position is also known along the axis Y of the probe 2. Therefore, there are at most as many first wave echo signals passing through the point P as there are pairs (i, j) of transmitter/receiver indices in the probe 2 (i.e. at most M×N signals if M is the number of transmitters used and N is the number of receivers used).

The estimation of the trajectories of ultrasonic waves is implemented by exploiting the Fermat principle, according to which it is assumed that a wave propagates rectilinearly in a homogeneous medium. Here, the body C comprising the non-bone biological tissue and the bone B is considered as a whole as a homogeneous medium. It is assumed that the propagation velocity of a wave is equal to the first candidate value considered, which corresponds to a credible value of sound propagation velocity in the non-bone biological tissue T.

In another embodiment, the construction step 200 of the first image is implemented using the so-called Reverse Time Migration (RTM) method. This method is an alternative imaging method resulting in an image representing the reflectivity of a region at any point on it. It assumes knowledge of the geometry of the medium under study and the velocity of wave propagation at each point. The reflectivity image is obtained by calculating, at any point in the image, a temporal correlation between an incident field generated by a transmitter and the backpropagated field recorded by the receivers. These fields are obtained by numerically solving the acoustic (or elastic) wave equation, using respectively the waveform generated by a transmitter and the echo signals recorded by the receivers (reversed in time) as boundary conditions. These operations must be repeated for each emission. The final image is obtained by summing the images obtained for each program. However, this method is much more time-consuming in terms of calculation time than the preferred embodiment described above.

The processor 8 then calculates propagation times of the waves passing through the point P via the estimated paths.

A propagation time is the sum of a propagation time $t_T(i, P)$ from the transmitter of index i to the point P and of a propagation time $t_R(j, P)$ from the point P to the receiver of index j.

The processor 8 then calculates an intensity of a pixel of the first image at the point P from the estimated propagation times, the first echo signals and the positions of the transmitters and receivers.

The intensity I of the point P is typically calculated using the formula below:

$$I(P) = \sum_{i=1}^{M} \sum_{j=1}^{N} W(P, i, j) \times D(t = t_T(i, P) + t_R(j, P), i, j)$$

wherein:
- $D(t=t_T(i,P)+t_R(j,P),i,j))$ is data representative of an echo signal received at time t by the receiver of index j, the echo being from a wave initially transmitted by the transmitter of index i,
- W(P, i, j) is a weight obtained by applying a predetermined weighting function W.

Typically, the weighting function W is an observation window function (also called a weighting or apodization window in the literature). Therefore, W(P, i, j)=1 if the angle of the return path segment of the wave from the point P to the receiver of index j, relative to a direction normal to a transmission/reception plane of the probe 2, is less than a predetermined angular threshold, else W(P, i, j)=0. This angular threshold is for example fixed at 50 degrees (this angle corresponds to a loss of sensitivity of a receiver of the order of 50%).

By repeating the above substeps at several points P, a first image can be reconstructed. The construction step 200 of a first image is then completed.

The construction step 200 of a first image is repeated for each first value stored in the memory 10.

Figure 5A:
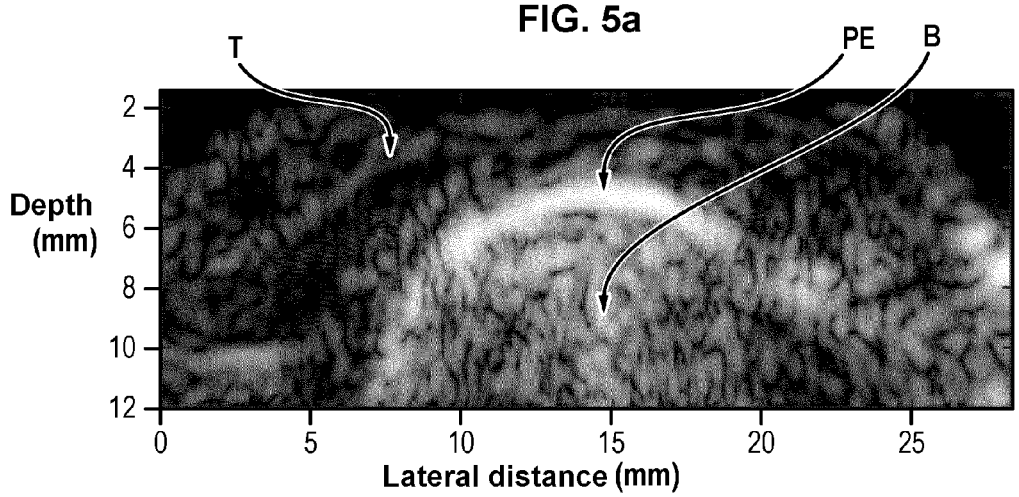
FIGS. 5a and 5b are two examples of images constructed during the implementation of the method according to the first embodiment of the invention.

FIG. 5a shows an example of the first image that can be obtained through the implementation of the construction step 200. As can be seen, this first image is relatively rich in information at the level of the non-bone biological tissue T surrounding the bone. On the other hand, this first image is poor in information inside the bone. The first image shows a blurred area at the bone B in particular. This is due to the fact that the processor 8 has taken as its reference propagation velocity a first candidate value which corresponds to a credible value of sound propagation velocity in the non-bone biological tissue T, but which does not correspond to a credible value of sound propagation velocity in bone, as discussed in the introduction of the present disclosure.

Returning to FIG. 4, for a first image constructed in step 200, the processor 8 calculates a first metric representative of a focus quality in a region of interest in the first image (step 202). The region of interest selected is typically a region showing the periosteum PE and/or non-bone biological tissue T surrounding the bone B.

The first metric is preferably a function of average intensity and/or average contrast in the region of interest considered in the first image.

The first metric is typically one or a combination of the following metrics, known to the prior art:
- The lateral spectral energy metric described in "Sound Velocity Correction in Ultrasound Imaging" by D. Napolitano, C. Chou, G. McLaughlin et al. published in 2006,
- the "Brenner sharpness criteria metric" or "Tenenbaum sharpness criteria metric" or "variance-based sharpness criteria metric", all described in "Automatic sound velocity selection in photoacoustic image reconstruction using an autofocus approach," by B. Treeby, T. Varslot, E. Zhang et al. published in 2011.

The processor 8 repeats step 202 for each first image constructed in step 200. The processor 8 thus generates as many first metrics as first images, and as many first predetermined candidate values.

The processor 8 then selects as the final value for the velocity $V_{tissue1}$ an optimal value among the first candidate values used to produce the first images (step 204). The processor 8 uses the first metrics to do this.

The first candidate value selected as velocity $V_{tissue1}$ in step 204 is the one used as input to produce a first image whose associated metric is indicative of a focus quality in the region of interest that is the highest among all first calculated metrics. Typically, when one of the methods listed above is used to calculate the first metric, the first metric of maximum value is searched for among the first calculated metrics.

The real velocity $V_{tissue1}$ was thus determined in the non-bone biological tissue of the body C being studied. Step 104 is then complete.

Returning to FIG. 3, the processor 8 also locates a first demarcation curve between the non-bone biological tissue and the bone B in one of the first constructed images (step 106). In practice, this demarcation curve is located at the level of a zone of the image of high intensity, corresponding to the periosteum PE.

Very preferentially, the localization 106 is implemented in the first image constructed using the first candidate value selected as the velocity $V_{tissue1}$. The localization is then much more precise due to the high focus quality of this first image among all those constructed by the processor 8.

The localization 106 conventionally consists of the following steps:

the first image is segmented in order to identify a group of pixels of the first image showing the boundary between the non-bone biological tissue and the bone B (this segmentation comprising for example the implementation of a Djikstra algorithm known from the prior art);

this group of pixels is approximated to a demarcation curve defined by a polynomial, for example a parabola.

The processor 8 then determines the velocity $V_{bone1}$ (step 108) by advantageously exploiting the first demarcation curve located in step 106, and the velocity $V_{tissue1}$ otherwise determined in step 104.

Figure 6:
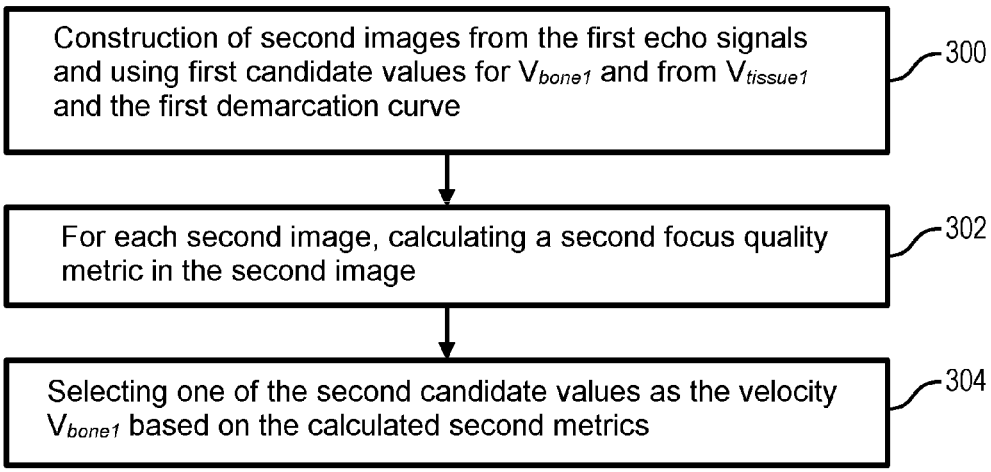

With reference to FIG. 6, the determination 108 of the velocity $V_{bone1}$ includes the following steps.

For each of the second candidate values stored in the memory 10, the processor 8 constructs a second image showing cortical bone tissue of the bone B and the endosteum E, from the first echo signals, the velocity $V_{tissue1}$ and the first demarcation curve, and under the assumption that the velocity $V_{bone1}$ is equal to the second candidate value (step 300).

The construction 300 of a second image from a second candidate value involves the implementation of substeps similar to those of the construction 200 of a first image, with a few differences.

Like step 200, step 300 can use the Kirchhoff migration method or the Total Focusing Method.

In this case, an estimation of wave trajectories passing through a point P is again implemented, again using the Fermat principle, according to which it is assumed that a wave propagates rectilinearly in a homogeneous medium. However, the body C is this time considered during the implementation of this trajectory estimation as a heterogeneous medium: the non-bone biological tissue is considered as a first homogeneous medium, in which the first ultrasonic waves propagated at the velocity of $V_{radial\_tissue}$ determined in advance. On the other hand, bone B is considered a second medium in which these first waves propagated to one of the second candidate values. The demarcation curve is thus an interface line between the two media, in which a wave undergoes refraction.

By combining these assumptions with the previously localized demarcation curve, it is thus possible to estimate during the construction 300 of a second image the trajectories of first ultrasonic waves not only passing through a point P located in the non-bone biological tissue, but also the trajectories of first waves that have passed through a point P located in the bone B.

Alternatively, the construction step 300 of the second image is implemented using RTM.

Figure 7:
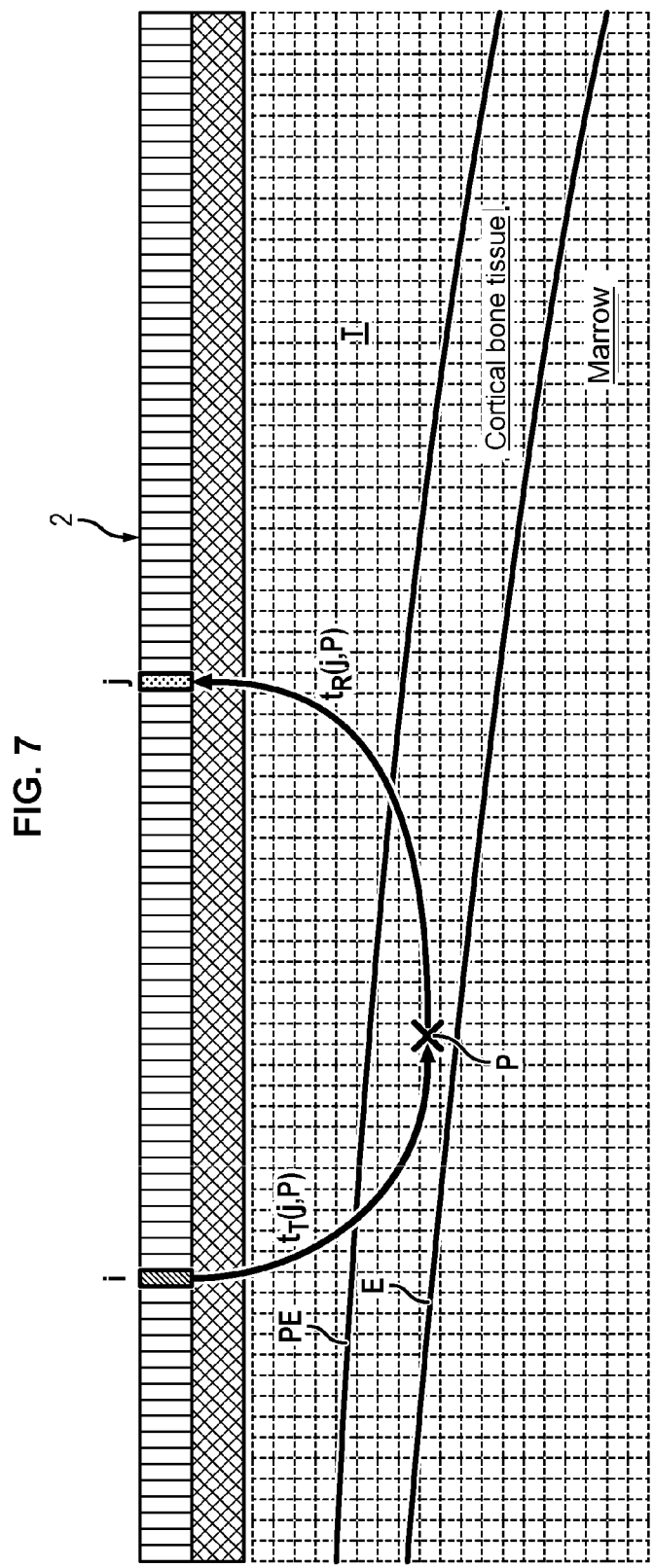
FIG. 7 is a longitudinal section plane of a body containing bone, also showing the path of an ultrasonic wave in this body.

FIG. 7 shows an example of the trajectory of a compressional ultrasonic wave from the transmitter 6 of index i to the receiver 6 of index j, passing through a point P of the bone (more precisely at the cortical tissue of the bone), which was estimated at step 300. This estimated trajectory is continuous in pieces and comprises the following four successive segments:

a first segment in the non-bone biological tissue T up to a first point of the second demarcation curve, a second segment extending the first segment from the second demarcation curve to the point P, the second segment being non-parallel to the first segment due to the refraction of the wave as it changes medium at the first point of the second demarcation curve, a third segment from the point P to another point on the second demarcation curve, and a fourth segment starting from the second point of the second demarcation curve and going towards the receiver of index j, the fourth segment being non-parallel to the third segment due to the refraction of the wave when it changes its medium again at the second point of the second demarcation curve.

In construction step 300 of a second image, the processor 8 then calculates propagation times of the ultrasonic waves via the estimated paths and pixel intensities from the propagation times, the first echo signals and the positions of the transmitters and receivers in the same way as described in the construction of one of the first images.

Here, the propagation time $t_T(i, P)$ from transmitter of index i to the point P covers the first and second segment, and the propagation time $t_R (j; P)$, i, j from the point P to the receiver of index j covers the third and fourth segments.

Ultimately, the construction 300 of a second image uses essentially the same principles as the construction 200 of a first image, but uses more input data, especially the demarcation curve, allowing the second images to show usable information at the bone B.

Figure 5B:
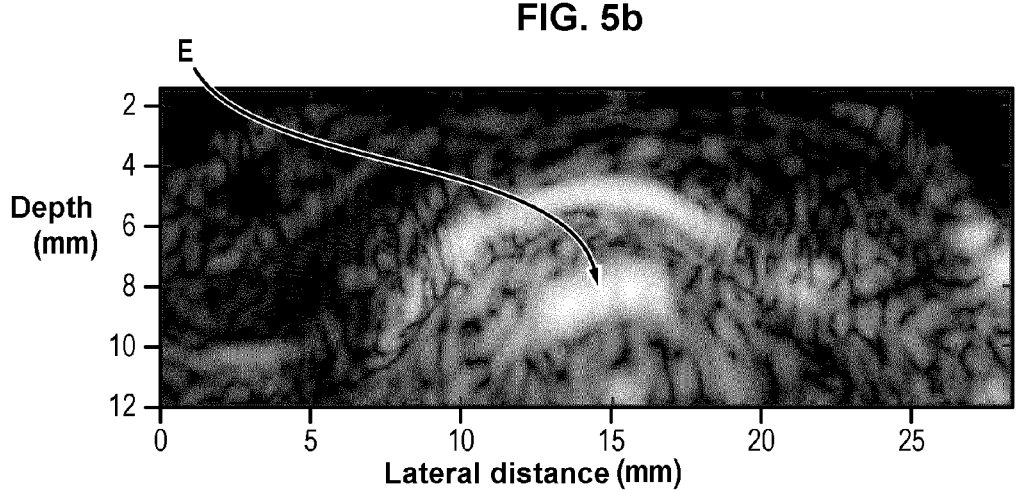

FIG. 5b shows an example of a second image that can be obtained through the implementation of construction step 300. As can be seen, this second image is relatively rich in information not only at the level of the non-bone biological tissue T surrounding the bone B, but also within the bone B, at the periosteum PE and at the endosteum E.

The processor 8 then calculates, for each second image, at least one second metric indicative of a focus quality of the cortical bone tissue of the bone B and/or of the endosteum E of the bone B in the second image (step 302). The third metrics are for example of the same type as the first metrics.

The processor 8 then selects as the final value for the velocity $V_{bone1}$ an optimal one of the second candidate values used to produce the second images (step 304). The processor 8 uses the second metrics for this, in the same way as in step 204.

Figure 8:
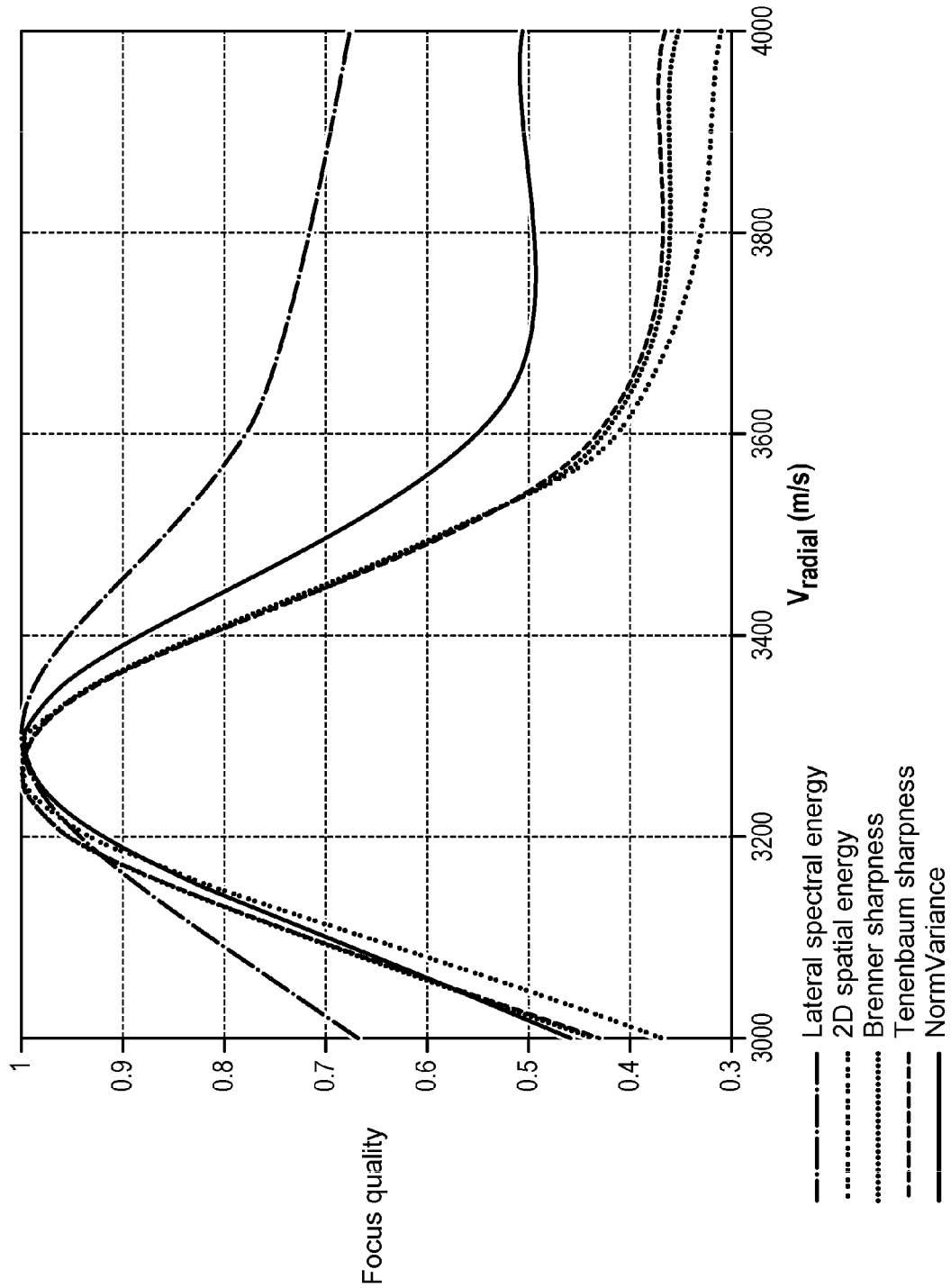
FIG. 8 is a set of curves, each curve showing the evolution of a metric calculated during the implementation of the method according to the first embodiment of the invention, as a function of a candidate value of the propagation velocity of radial compressional waves in a bone.

FIG. 8 shows different second metric curves according to the second candidate value used. It can be seen that whatever method is used to calculate the second metric, the second value selected as velocity $V_{bone1}$ is approximately the same (the maxima of these curves are indeed very close to each other).

The real velocity $V_{bone1}$ was thus determined in the bone B of the body C being studied. Step 108 is then complete.

This velocity $V_{bone1}$ is in itself an interesting piece of data as it can be used as an input to diagnose a possible osteoporosis of the bone B of the body C being studied.

Figure 9:
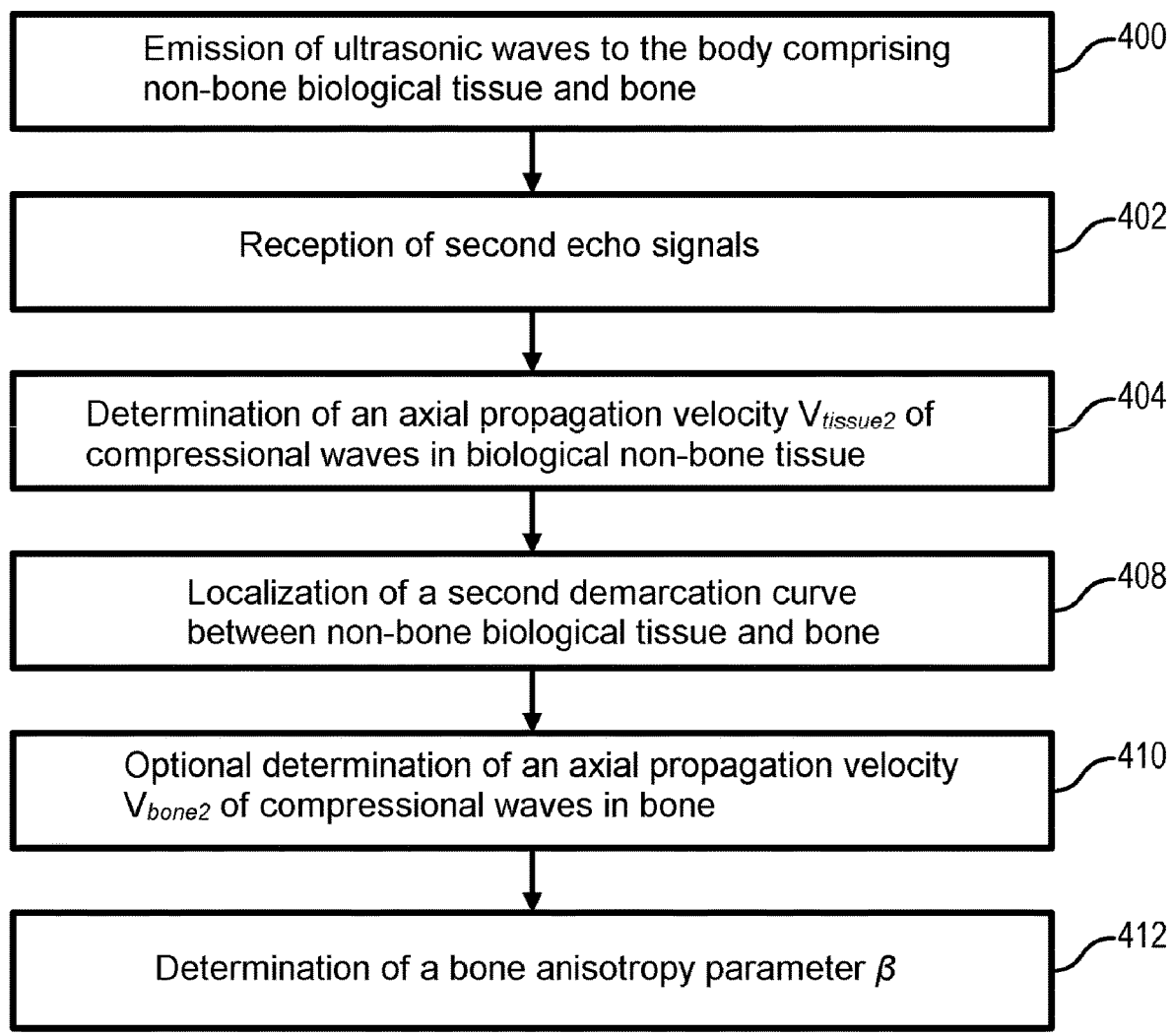
FIG. 9 shows further steps in the method for characterizing a bone according to the first embodiment of the invention.

However, it is advantageous to supplement this information with other velocities in order to characterize more fully the bone B under study. To this end, the method implemented by the system 1 for characterizing bone B comprises the following additional steps, with reference to FIG. 9.

The probe 2 is positioned close to the body C in a second position different from the first position. In the second position, the transceivers 6 of the probe 2 are aligned in a second direction different from the first direction.

The probe 2 emits second ultrasonic waves to the body C in the second direction (step 400).

The second waves are preferably axial compressional waves. In other words, the second direction is, for example, in a plane including the longitudinal axis of the bone B. This second direction is preferably substantially parallel to the longitudinal axis of the bone, i.e. forms an angle α with the longitudinal axis of the bone B which is less than 20 degrees.

The second ultrasonic waves penetrate the body C and are reflected by it at different depths into the body C.

New echo signals of these second waves, so-called second echo signals, are thus acquired by the transceivers 6 of the probe 2 (step 402).

The echo signals are digitized, transmitted to processing device 4 and stored in the memory 10.

If necessary, the processor 8 then determines, based on second echo signals, the velocity $V_{bone2}$ (step 410).

The step 410 of determination the velocity $V_{bone2}$ can be implemented using a known method of the prior art based on the identification of a head wave propagating along the outer surface of the bone B.

This known technique uses two specific second echo signals acquired in response to the emission of waves from two end transmitters 6 of the probe 2 (typically, that of the 0 index and that of the maximum index). All transceivers 6 receive the waves selectively emitted by one of the end transmitters 6 of the probe 2. The distance between the two end transmitters 6 is known, typically between 10 and 40 mm. At this scale, it can be assumed that the outer surface of the bone B is flat. Therefore, the propagation velocity of a head wave along this surface can be easily determined since the relationship between the time of arrival of the head wave of a wave by one of the two transceivers 6 used and the distance between one of the two end transmitters 6 and the receivers 6 is a linear function. Under this assumption of linearity, it is very easy to determine:

the velocity V1 of a head wave that propagated along the bone B when the transceiver 6 of index 0 was used as a transmitter, and all the transceivers 6 were used as receivers, and the velocity V2 of a head wave that propagated along the bone B when the highest index transceiver 6 was used as a transmitter, and all the transceivers 6 were used as receivers.

Velocity $V_{bone2}$ is then calculated by the processor 8 using the following formula:

$$V_{bone2} = \frac{2V_1 V_2 \cos(\alpha)}{V_1 + V_2}$$

In addition, the processor 8 determines the velocity $V_{tissue2}$ based on the second echo signals (step 404). This step uses the same basic principles as step 104, which determined the velocity $V_{tissue1}$, the difference being that step 404 uses the second waves that were emitted while the probe 2 was in the second position and not the first position.

Figure 10:
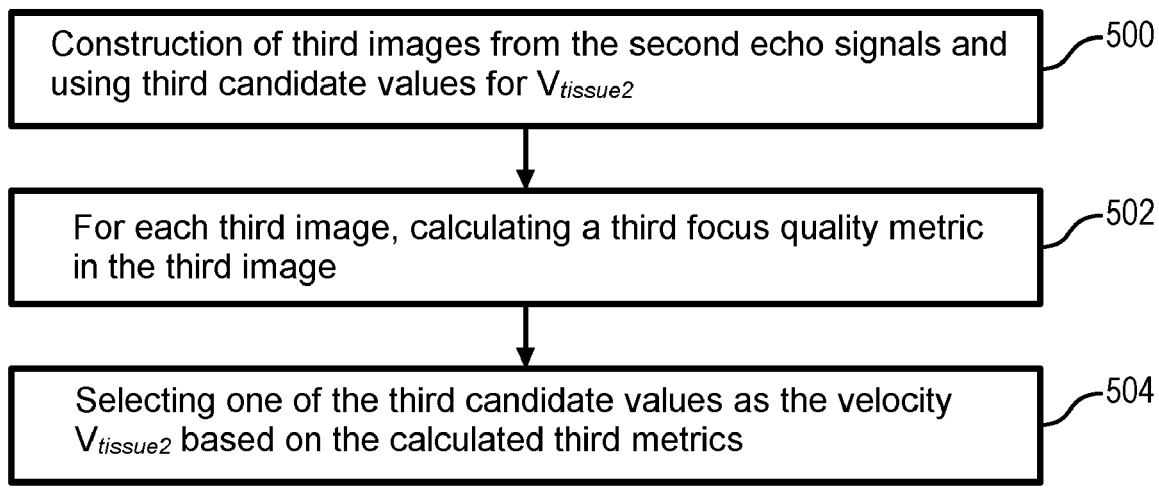
FIGS. 10 and 11 detail substeps of the steps shown in FIG. 9.

The determination 404 of the velocity $V_{tissue2}$ includes more specifically the following steps, with reference to FIG. 10:

for several third candidate values, construction of a third image showing the biological tissue and the periosteum PE of the bone, based on the second echo signals and under the assumption that the velocity $V_{tissue2}$ is equal to the second candidate value (step 500), for each third image, calculation of a third metric indicative of the focus quality of the periosteum PE in the third image (step 502), selection of one of the third candidate values as velocity $V_{tissue2}$, based on third metrics (step 504).

The third images are views of the body C in a longitudinal section parallel to the axis X of the bone B.

The third metrics are for example of the same type as the first metrics and/or the second metrics.

Returning to FIG. 9, the processor 8 localizes a second demarcation curve between the non-bone biological tissue and the bone B in one of the third constructed images (step 408).

Very preferentially, the localization 408 of the second curve is implemented in the third image constructed using the third candidate value selected as velocity $V_{tissue2}$. The localization is then much more precise due to the high focus quality of this third image among all those constructed by the processor 8 during step 500.

The processor 8 also determines the parameter β of anisotropy of the bone B studied (step 412).

As previously mentioned, this parameter β can be used by the predetermined function V in combination with the velocity $V_{bone1}$ and with the velocity $V_{bone2}$ to calculate a propagation velocity V(θ) of a compressional wave in the bone B in any direction forming an angle θ with the axis X.

Figure 11:
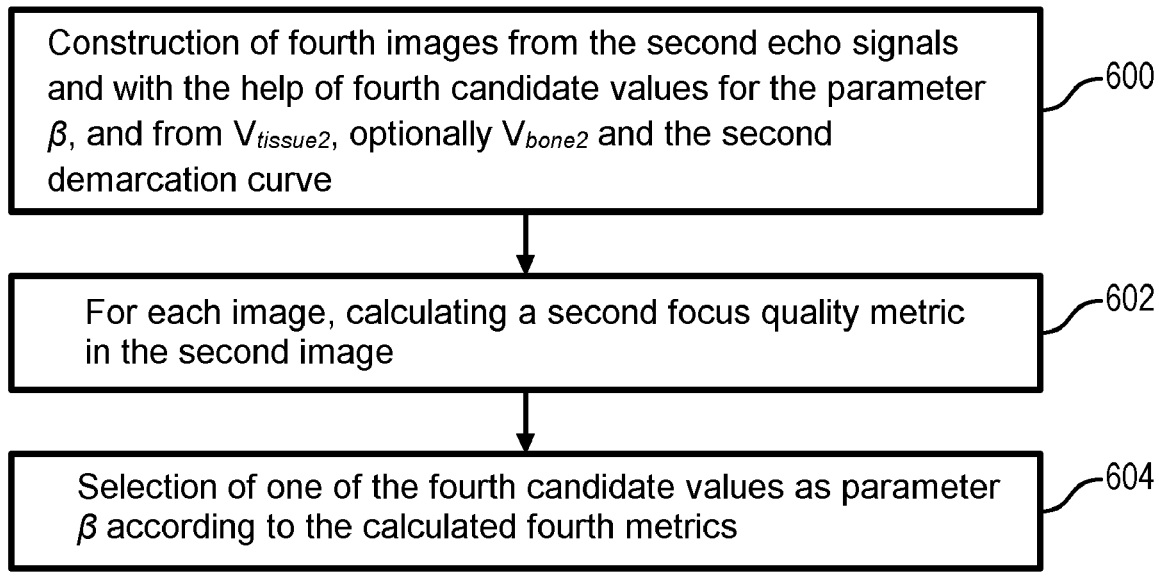

The parameter β of anisotropy of the bone B is determined in step 412 using the following substeps with reference to FIG. 11.

For each fourth candidate value stored in the memory 10, the processor 8 constructs a fourth image showing cortical bone tissue and the endosteum E of the bone, from the second echo signals, the velocity $V_{bone1}$ velocity $V_{bone2}$ of the predetermined function V, and under the assumption that the anisotropy parameter of the bone B β is equal to the fourth candidate value (step 600).

This step 600 is similar to steps 200, 300 and 500 in that it can use one of the Kirchhoff migration methods or the Total Focusing Method. It should simply be noted that the wave trajectories estimated in step 600 are based in this case on the assumption that the propagation velocity of a wave in the bone B observed in any direction respects the model defined by the function V. Alternatively, construction step 300 of the second image is implemented using RTM.

Thus, after step 600, a plurality of fourth images is obtained, one for each fourth candidate value initially stored in the memory 10.

For each fourth image, the processor 8 calculates at least one fourth metric indicative of a focus quality of the endosteum E and/or of the biological tissue T surrounding the bone B in the fourth image (step 602). The fourth metrics, for example, are of the same type as the first metrics.

The processor 8 then selects one of the fourth candidate values as anisotropy parameter the bone B, β, based on the fourth metrics (step 604).

Figure 12:
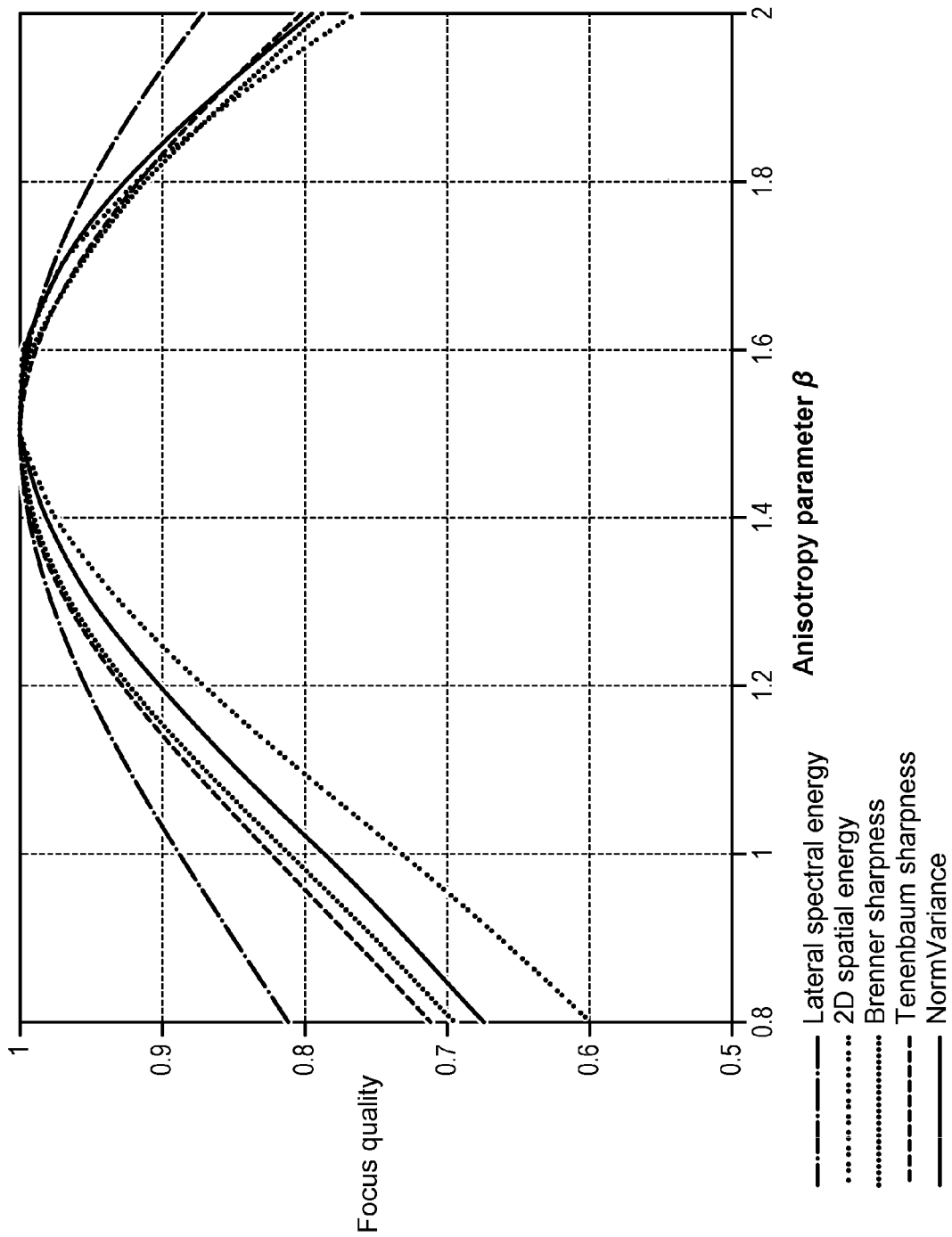
FIG. 12 is a set of curves, each curve showing the evolution of a metric calculated during the implementation of the method according to the first embodiment of the invention, as a function of a candidate value for a parameter of anisotropy of a bone.

FIG. 12 shows different fourth metric curves according to the fourth candidate value used. It can be seen that regardless of the method used to calculate the fourth metric, the fourth value selected as parameter β is more or less the same (the maxima of these curves are indeed very close to each other), as was also the case for the velocity $V_{bone1}$.

It is now possible for the processor 8 to calculate any propagation velocity of a compression wave in the bone B using the function V parameterized with the data $V_{bone1}$, $V_{bone2}$ and β determined during the process.

In the embodiment of the method just described, the various characteristic data of the bone B, which are $V_{bone1}$, $V_{bone2}$ and β were determined in separate steps, not jointly. In particular, determination steps 104, 108 and 412 each used only one set of candidate values (second candidate values for step 104, third candidate values for step 108, fourth candidate values for step 412). This ultimately limits the number of second, third and fourth images constructed.

In other words, the material resources (computing load, memory 10) required to implement these steps are relatively moderate.

Advantageously, the processor 8 controls a display screen 12 at least one of the following images:
- the first image constructed using the first value selected in step 204,
- the second image constructed using the second value selected in step 304,
- the third image constructed using the first value selected in step 504,
- the second image constructed using the second value selected in step 604.

These images have a high focus quality and are therefore of interest to a practitioner.

The invention is not limited to the only embodiment which has just been described in relation to the figures.

The invention is particularly applicable to the study of shear waves.

In this case, it is possible to model the propagation velocity of a shear wave in the bone B using the predetermined function V of the following form:

$$V(\theta) = V_{bone1}[1 + \beta \sin^2(\theta) \cos^2(\theta)]$$

where
- $V_{bone1}$ is a propagation velocity of a shear wave in the bone B in a first direction parallel to the longitudinal axis X,
- $\theta$ is any angle,
- $V(\theta)$ is a propagation velocity of a shear wave in the bone B in a direction forming the angle $\theta$ with the first direction.

Figure 13:
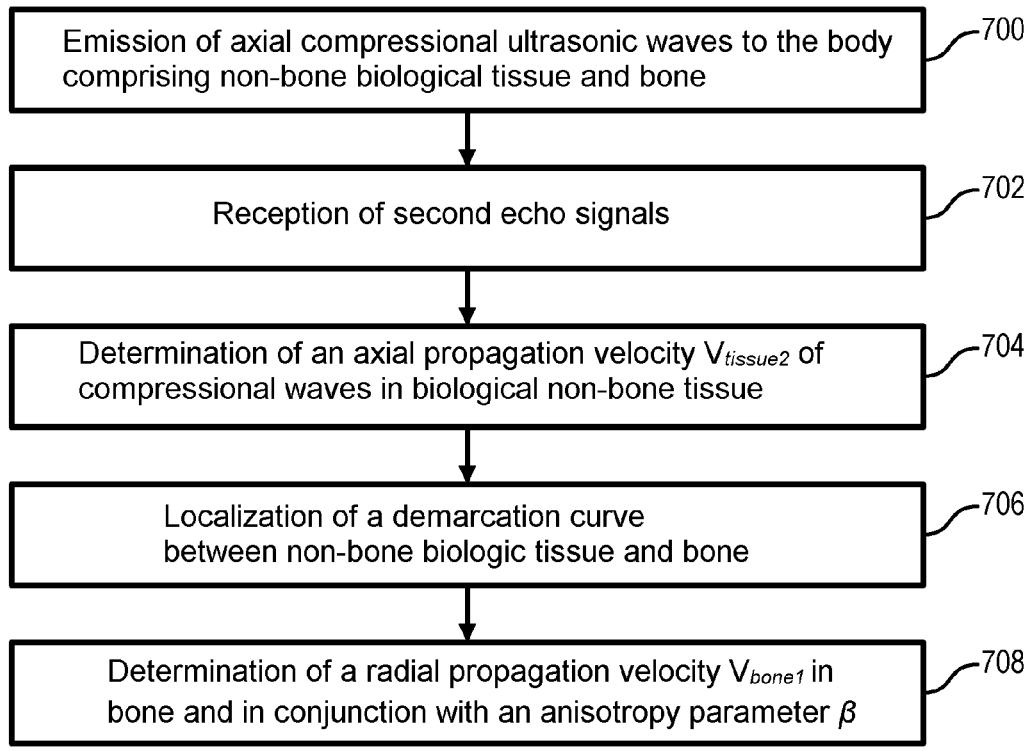
FIG. 13 is a flowchart of the steps in a method for characterizing a bone, according to a second embodiment of the invention.

For example, FIG. 13 shows a flowchart of the steps in a bone characterization method according to a second embodiment.

The probe 2 is positioned in the second position described above, and ultrasonic compression waves are emitted by the probe 2 in this second position (step 600).

In a manner known per se, the emitted compressional waves cause shear waves to appear in the bone B. These shear waves are generated when the compression waves penetrate the cortical bone tissue of the bone B, located between the periosteum PE and the endosteum E.

Echo signals from these shear waves are then received by the probe 2 (step 602).

The processor 8 then determines a velocity $V_{tissue2}$ of axial propagation of compressional waves in non-bone biological tissue T (step 704). This step 704 is similar to step 504.

The processor 8 locates a demarcation curve between the tissue T and the bone B (step 706). This step is identical to step 408.

Figure 14:
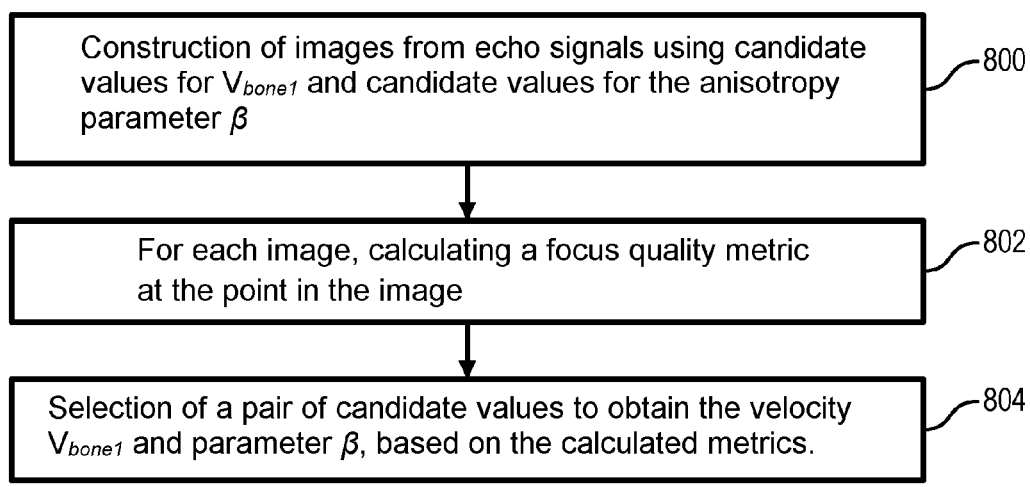
FIG. 14 details substeps of a method step according to the second embodiment of the invention.

The processor 8 then determines the velocity $V_{bone1}$ (step 708) in the bone B, and, in conjunction, the anisotropy parameter $\beta$. This joint determination includes the following substeps, with reference to FIG. 14.

It is assumed that a set of second candidate values has been previously stored in the memory, for the velocity $V_{bone1}$. These second values are between 1300 and 2000 metres per second for shear waves in the bone.

Moreover, the fourth candidate values are, in this embodiment, between −0.3 and 0.3 for the anisotropy parameter $\beta$ of the shear waves in the bone.

For a pair consisting of a fourth candidate value (for $\beta$) and a second candidate value, the processor constructs an image from the echo signals, making the dual assumption that the velocity $V_{bone1}$ is equal to the second candidate value of the pair, and that the anisotropy parameter $\beta$ is equal to the fourth value of the pair (step 800).

The processor 8 repeats this step 800 for each available pair.

It can be seen here that the number of constructed images is much greater than the number of images generated in one step of the method according to the first embodiment, because one works in two dimensions instead of just one.

For each constructed image, the processor calculates a focus quality metric (step 802). This step is similar to steps 502, 602.

The processor 8 then selects one of the pairs used to construct the images in step 800 (step 804), based on the calculated metrics. This step is similar to steps 504, 604.

The invention claimed is:

1. A method comprising:
   transmitting ultrasonic waves to a body comprising a bone and non-bone biological tissue surrounding the bone, wherein the bone comprises a periosteum, an endosteum and cortical bone tissue,
   receiving echo signals of the ultrasonic waves,
   constructing first images from the echo signals and from first candidate values, wherein each first image shows the non-bone biological tissue and the periosteum, and is constructed by assuming that a sound velocity in the non-bone biological tissue in a direction is equal to one of the first candidate values,
   computing first metrics from the first images, wherein each first metric is indicative of a focus quality of the periosteum and/or the non-bone biological tissue in one of the first images,
   based on the first metrics, selecting one of the first candidate values as the sound velocity in the non-bone biological tissue in the direction,
   localizing a demarcation curve between the non-bone biological tissue and the bone in one of the first images,
   constructing second images from the echo signals, from the sound velocity in the non-bone biological tissue in the direction, from the demarcation curve and from second candidate values, wherein each second image shows the cortical bone tissue and the endosteum, and wherein each second image is constructed by assuming that a sound velocity in the bone in the direction is equal to one of the second candidate values,
   computing second metrics from the second images, wherein each second metric is indicative of a focus quality of the cortical bone tissue of the bone and/or the endosteum in one of the second images,
   based on the second metrics, selecting one of the second candidate values as the sound velocity in the bone in the direction.

2. The method of claim 1, wherein constructing the first images comprises:
   estimating trajectories of the ultrasonic waves which were transmitted by transmitters, which passed through a point of the non-bone biological tissue then were received by receivers, from the echo signals and by assuming that the sound velocity in the non-bone biological tissue in the direction is equal to one of the first candidate values,
   calculating propagation times of the ultrasonic waves via the trajectories,
   calculating an intensity of a pixel of one of the first images at the point of the non-bone biological tissue, from the propagation times, the echo signals, positions of the transmitters and positions of the receivers.

3. The method of claim 1, wherein constructing the second images comprises:
estimating trajectories of the ultrasonic waves which passed through a point of the bone, then were received by receivers, from the echo signals, from the sound velocity in the non-bone biological tissue in the direction, from the demarcation curve, and by assuming that the sound velocity in the bone in the first direction is equal to one of the second candidate values,
calculating propagation times of the ultrasonic waves via the trajectories,
calculating an intensity of a pixel of one of the second images at the point of the bone from the propagation times, the echo signals, positions of the transmitters and positions of the receivers.

4. The method of claim 1, wherein localizing the demarcation curve is localized in the first image which has been constructed from the selected first candidate value.

5. The method of claim 1, wherein the ultrasonic waves are transmitted by transmitters and the echo signals are received by receivers aligned along an axis perpendicular to a longitudinal axis of the bone, and wherein the direction is perpendicular to the longitudinal axis of the bone.

6. The method of claim 1, further comprising displaying the first image constructed from the selected first candidate value and/or the second image constructed from the selected second candidate value.

7. The method of claim 1, further comprising:
transmitting other ultrasonic waves to the body,
receiving other echo signals of the other ultrasonic waves,
constructing third images from third candidate values and from the other echo signals, wherein each third image shows the non-bone biological tissue and the periosteum of the bone, and wherein each third image is constructed by assuming that the sound velocity in the non-bone biological tissue in the another direction is equal to one of the third candidate values,
computing third metrics from the third images, wherein each third metric is indicative of a focus quality of the periosteum and/or of the non-bone biological tissue in one of the third images,
based on the third metrics, selecting one of the third candidate values as the sound velocity in the non-bone biological tissue in the another direction,
localizing another demarcation curve between the non-bone biological tissue and the periosteum in one of the third images,
determining a sound velocity in the bone in the another direction from the other echo signals,
constructing fourth images from fourth candidate values, from the other echo signals, from the sound velocity in the bone in the direction, from the sound velocity in the non-bone biological tissue in the another direction, from the another demarcation and from a predetermined function, wherein each fourth image shows cortical bone tissue and the endosteum, and wherein each fourth image is constructed by assuming that an anisotropy parameter of the bone is equal to one of the fourth candidate values, wherein the predetermined function is configured to calculate a sound velocity in the bone in any direction from the anisotropy parameter of the bone, from the sound velocity in the bone in the direction and from the sound velocity in the bone in the another direction,
computing fourth metrics from the fourth images, wherein each fourth metric is indicative of a focus quality of the endosteum and/or the cortical bone tissue of the bone in one of the fourth images,
based on the fourth metrics, selecting one of the fourth candidate values as the anisotropy parameter of the bone.

8. The method of claim 7, wherein constructing the fourth images comprises:
estimating trajectories of the other ultrasonic waves which were transmitted by transmitters, then passed through a point of the bone, then were received by receivers, from the other echo signals, the sound velocity in the non-bone biological tissue in the another direction, the sound velocity in the bone in the direction, the another demarcation curve, the predetermined function, and by assuming that the anisotropy parameter of the bone is equal to one of the fourth candidate values,
calculating propagation times of the other ultrasonic waves via the trajectories,
calculating an intensity of a pixel of one of the fourth images at the point of the bone, from the propagation times, from the other echo signals, from positions of the transmitters and from positions of the receivers.

9. The method of claim 7, wherein the another demarcation curve is localized in the third image which has been constructed from the selected third candidate value.

10. The method of claim 7, further comprising displaying the third image constructed from the selected third candidate value and/or the fourth image constructed from the selected fourth candidate value.

11. The method of claim 7, wherein the other ultrasonic waves are transmitted by transmitters and the other echo signals are received by receivers aligned along an axis lying in a plane comprising a longitudinal axis of the bone.

12. The method of claim 1, wherein the sound velocity in the bone in the direction is a compressional wave propagation velocity or a shear wave propagation velocity.

13. The method of claim 7, wherein at least one of the sound velocity in the bone in the direction and the sound velocity in the bone in the another direction is a compressional wave propagation velocity, and wherein the predetermined function is a function V such that:

$$V(\theta)=V_{bone2}-(V_{bone2}-V_{bone1})[\beta \sin^2(\theta)\cos^2(\theta)+\cos^4(\theta)]$$

where
$V_{bone1}$ is the sound velocity in the bone in the direction,
$V_{bone2}$ is the sound velocity in the bone in the another direction,
$\beta$ is the anisotropy parameter of the bone,
$\theta$ is an angle,
$V(\theta)$ is a propagation velocity of compressional waves in the bone in a direction forming angle $\theta$ with the direction.

14. The method of claim 1, wherein the sound velocity in the bone in the first direction is a shear wave propagation velocity, and wherein the predetermined function is a function V such that:

$$V(\theta)=V_{bone1}[1+\beta \sin^2(\theta)\cos^1(\theta)]$$

where
$V_{bone1}$ is the sound velocity in the bone in the first direction,
$\beta$ is the anisotropy parameter of the bone,
$\theta$ is an angle,
$V(\theta)$ is a velocity of shear wave propagation in the bone in a direction forming angle $\theta$ with the direction.

15. The method of claim 1, wherein the second images are constructed from the second candidate values and from other candidate values, wherein each second image is constructed by assuming that an anisotropy parameter of the bone is equal to one of the other candidate values, and wherein the method further comprises:
  based on the second metrics, selecting one of the other candidate values as the anisotropy parameter of the bone.

\* \* \* \* \*